United States Patent
Mohl

(10) Patent No.: US 11,432,928 B2
(45) Date of Patent: Sep. 6, 2022

(54) IMPLANT AND METHOD FOR IMPROVING COAPTATION OF AN ATRIOVENTRICULAR VALVE

(71) Applicant: AVVIE GMBH, Vienna (AT)

(72) Inventor: Werner Mohl, Altenmarkt-Thennenberg (AT)

(73) Assignee: AVVIE GMBH, Vienna (AT)

(*) Notice: Subject to any disclaimer, the term of this patent is extended or adjusted under 35 U.S.C. 154(b) by 49 days.

(21) Appl. No.: 16/491,696

(22) PCT Filed: Feb. 27, 2018

(86) PCT No.: PCT/IB2018/000151
§ 371 (c)(1),
(2) Date: Sep. 6, 2019

(87) PCT Pub. No.: WO2018/162975
PCT Pub. Date: Sep. 13, 2018

(65) Prior Publication Data
US 2020/0268512 A1    Aug. 27, 2020

(30) Foreign Application Priority Data
Mar. 6, 2017  (EP) ..................... 17000331

(51) Int. Cl.
*A61F 2/24*  (2006.01)
(52) U.S. Cl.
CPC ............ *A61F 2/2463* (2013.01); *A61F 2/246* (2013.01); *A61F 2/2418* (2013.01);
(Continued)
(58) Field of Classification Search
CPC ...... A61F 2/2463; A61F 2/246; A61F 2/2442; A61F 2210/0014; A61F 2230/0006; A61F 2230/0013; A61F 2250/0069
See application file for complete search history.

(56) References Cited

U.S. PATENT DOCUMENTS

2006/0058871 A1* 3/2006 Zakay .................... A61F 2/246
                                                                 623/2.18
2011/0208298 A1   8/2011 Tuval et al.
(Continued)

FOREIGN PATENT DOCUMENTS

| WO | 2013/036742 | 3/2013 |
| WO | 2014207575 A2 | 12/2014 |
| WO | 2015052570 A1 | 4/2015 |

OTHER PUBLICATIONS

International Search Report received in PCT/IB2018/000151 dated May 16, 2018, pp. 13.

*Primary Examiner* — Jerrah Edwards
*Assistant Examiner* — Jared Klar Rovira
(74) *Attorney, Agent, or Firm* — Liang & Hennessey LLP; Brian Hennessey

(57) ABSTRACT

An implant for improving coaptation of an atrioventricular valve, the atrioventricular valve having a native first leaflet, a native second leaflet and an annulus and controlling blood flow from an upstream side to a downstream side of the valve, the implant comprising a support structure configured to be fixed to the annulus or to the native first leaflet, the implant further comprising a flexible artificial leaflet structure mounted to the support structure and comprising a rim section that is shaped to coapt with the native second leaflet, wherein said rim section comprises pockets that are open towards said downstream side and capable of being filled with blood from the downstream side each time the valve is closed.

21 Claims, 7 Drawing Sheets

(52) U.S. Cl.
CPC .......... *A61F 2/2427* (2013.01); *A61F 2/2442* (2013.01); *A61F 2/2466* (2013.01); *A61F 2210/0014* (2013.01); *A61F 2230/0006* (2013.01); *A61F 2230/0013* (2013.01)

(56) References Cited

U.S. PATENT DOCUMENTS

| | | | |
|---|---|---|---|
| 2014/0243968 A1* | 8/2014 | Padala | A61F 2/246 623/2.36 |
| 2016/0184098 A1* | 6/2016 | Vaturi | A61F 2/2445 623/2.17 |
| 2017/0049571 A1* | 2/2017 | Gifford, III | A61F 2/2454 |
| 2017/0252162 A1* | 9/2017 | Kuehn | A61F 2/2448 |

* cited by examiner

IMPLANT AND METHOD FOR IMPROVING COAPTATION OF AN ATRIOVENTRICULAR VALVE

CROSS-REFERENCE TO RELATED APPLICATIONS

This application is a national phase application of PCT Application No. PCT/IB2018/000151, filed Feb. 27, 2018, entitled "IMPLANT AND METHOD FOR IMPROVING COAPTATION OF AN ATRIOVENTRICULAR VALVE", which claims the benefit of European Patent Application No. 17000331.3, filed Mar. 6, 2017, each of which is incorporated by reference in its entirety.

FIELD OF THE INVENTION

The invention relates to an implant and a method for improving coaptation of an atrioventricular valve.

BACKGROUND

Atrioventricular valves are membranous folds that prevent backflow from the ventricles of the human heart into the atrium during systole. They are anchored within the ventricular cavity by chordae tendineae, which prevent the valve from prolapsing into the atrium.

The chordae tendineae are attached to papillary muscles that cause tension to better hold the valve. Together, the papillary muscles and the chordae tendineae are known as the subvalvular apparatus. The function of the subvalvular apparatus is to keep the valves from prolapsing into the atria when they close. The opening and closure of the valves is caused by the pressure gradient across the valve.

The human heart comprises two atrioventricular valves, the mitral valve and the tricuspid valve. The mitral valve allows the blood to flow from the left atrium into the left ventricle. The tricuspid valve is located between the right atrium and the right ventricle. The mitral valve has two leaflets that are each divided into several scallops: the anterior leaflet has three scallops (A1,A2,A3), the posterior leaflet has three scallops (P1,P2,P3). The tricuspid valve has three leaflets. Engagement of corresponding surfaces of the leaflets against each other is decisive for providing closure of the valve to prevent blood flowing in the wrong direction. The closure forms a so called coaptation area.

Native heart valves become dysfunctional for a variety of pathological causes. Failure of the leaflets to seal during ventricular systole is known as malcoaptation, and may allow blood to flow backward through the valve (regurgitation). Malcoaptation is often caused by a dilatation of the annulus. Annular dilatation mainly occurs in the mural part of the valve and the posterior leaflet, whereas the annulus of the anterior leaflet is part of the fibrous skeleton of the heart. Another reason is a restriction in motion or an excessive motion of the leaflet structures. Heart valve regurgitation can result in enlargement of the atria, atrial fibrillation and pulmonary hypertension, left and right heart failure, decreased blood flow, lower blood pressure, and/or a diminished flow of oxygen to the tissues of the body. Mitral and tricuspid regurgitation can also cause blood to flow back from the left or right atrium to the pulmonary veins or respective systemic veins, causing congestion and backward failure.

Some pathologies of atrioventricular valves, such as malcoaptation, often require reconstruction of the valvular and subvalvular apparatus as well as redesigning the enlarged annulus. Sometimes a complete surgical replacement of the natural heart valve with heart valve prosthesis is necessary. There are two main types of artificial heart valves: the mechanical and the biological valves. The mechanical-type heart valve uses a pivoting mechanical closure supported by a base structure to provide unidirectional blood flow. The tissue-type valves have flexible leaflets supported by a base structure and projecting into the flow stream that function similar to those of a natural human heart valve and imitate their natural flexing action to coapt against each other. Usually two or more flexible leaflets are mounted within a peripheral support structure made of a metallic or polymeric material. In transcatheter implantation the support within the annulus may be in the form of a stent, as is disclosed in US 2011/0208298 A1.

In order to provide enough space for the artificial leaflets to work properly, the peripheral support is positioned in the native valve so as to force the native leaflets apart. In order to provide appropriate anchoring of the peripheral support within the native valve, the same is fixed to the native leaflets by suitable means. However, in some applications, such as with mitral valves, fixing the peripheral support to the native anterior leaflet and dislocating the same from its natural position may cause an obstruction of the outflow tract and of the aortic valve, which is located in the left ventricle immediately adjacent the anterior leaflet.

The gold standard for treating mitral regurgitation in most pathologies is to repair the mitral apparatus including leaflets and the subvalvular apparatus and to reshape the mitral annulus in open heart surgery (Carpentier technique). If repair is not possible an excision of the valve including at least parts of the subvalvular apparatus is performed with subsequent implantation of a heart valve prosthesis. This is necessary particularly when the valve is destructed by inflammation. Although in most instances a complete excision of the destroyed valve is necessary, sometimes a partial replacement is possible. A clinically used mitral valve restoration system (Mitrofix®) replaces only the posterior leaflet with a rigid prosthesis mimicking a fixed posterior leaflet allowing the natural anterior leaflet to coapt. This prosthesis is also sewn into the position of the destroyed posterior aspect of the annulus. This requires open heart surgery and extended cardiac arrest.

Recent trends focus on less invasive procedures to minimize surgical trauma and to perform transcatheter approaches including transatrial, transaortal or transapical procedures to replace or reconstruct dysfunctional valves thus minimizing the need of or avoiding heart lung machine and cardiac arrest. Whereas this is a common procedure in aortic valves nowadays, only few mitral valves insufficiencies are corrected by percutaneous or transapical procedures. Most of these concepts are redesigning and remodeling artificially the mitral annulus to allow coaptation or to enforce coaptation by fixing both leaflets together with a clip (Mitral Clip®) reducing mitral regurgitant flow. Percutaneously or transapically deployed valve prostheses are difficult to anchor due to the special anatomy of the mitral valve and the vicinity of the anterior leaflet to the aortic outflow tract.

Artificial extension of the leaflet has been described in WO 2013/036742 A1. An inflatable plug is implanted on one or more of the mitral leaflets under 3D echocardiographic guidance. The position and size of the plug are then adjusted until mitral regurgitation is completely eliminated.

SUMMARY

Therefore, it is an object of the instant invention to provide an improved implant for improving coaptation of an atrioventricular valve. In particular, it is an object of the invention to provide an implant that does not involve the risk of stenosis of the aortic outflow tract and does not require cinching of the annulus thus preventing force to the dilated myocardium.

It is a further object of the invention to provide an implant that can be easily deployed to the target site.

It is a further object of the invention to use preoperative imaging data to construct a posterior leaflet according to the patient's pathologic anatomy.

The invention generally provides improved medical implants and methods for the treatment of regurgitation in atrioventricular valves, in particular mitral valves. In some embodiments, the invention provides a medical implant that provides replacement of one of the two or three native leaflet parts of atrioventricular valves, while leaving the other native leaflet(s) fully functional. In case of an implant configured for mitral valves, the medical implant preferably provides replacement of the native posterior leaflet, while leaving the native anterior leaflet fully functional. Preferably, the implant although being fixed to the mitral annulus circumferentially does not comprise any structure that is fixed to the anterior leaflet. When configured for the mitral valve, the implant preferably affects only one half of the valve, and only extends over the region of the posterior leaflet.

In the context of the instant invention, the terms "replacement" and "replacing" mean that the artificial leaflet replaces the function of a damaged or otherwise malfunctional native leaflet. However, the damaged or otherwise malfunctional native leaflet must not necessarily be physically removed. Rather, the damaged or otherwise malfunctional native leaflet may be left in the valve. The damaged or otherwise malfunctional native leaflet may be at least partially displaced by the artificial leaflet of the invention. Further, the damaged or otherwise malfunctional native leaflet may support the function of the artificial leaflet.

In some embodiments, the artificial leaflet is flexible in order to allow the artificial leaflet to behave like the artificial leaflet it replaces. In particular, the artificial leaflet is flexible at least in its lower end region, i.e. the end region facing the ventricular cavity.

In some embodiments, the invention provides an implant for improving coaptation of an atrioventricular valve, the atrioventricular valve having a native first leaflet, a native second leaflet and an annulus and controlling blood flow from an upstream side to a downstream side of the valve, the implant comprising a support structure configured to be fixed to the annulus or to the native first leaflet, the implant further comprising a flexible artificial leaflet structure mounted to the support structure and comprising a rim section that is shaped to coapt with the native second leaflet, wherein said rim section comprises pockets that are open towards said downstream side and capable of being filled with blood from the downstream side each time the valve is closed and allow washout during opening of the valve.

In case of an implant configured for mitral valves, the first native leaflet is a posterior leaflet of the mitral valve and the second native leaflet is an anterior leaflet of the mitral valve. The artificial leaflet is configured as an artificial posterior leaflet and replaces and/or supports the function of the native posterior leaflet. The artificial posterior leaflet is preferably shaped such as to improve coaptation with the native anterior leaflet.

In case of an implant configured for tricuspid valves, the first native leaflet is an anterior leaflet of the tricuspid valve and the second native leaflet is a posterior leaflet and the third leaflet is the septal leaflet of the tricuspid valve. The artificial leaflet is configured to replace the function of the native anterior and/or posterior leaflet. The artificial anterior or posterior leaflet or the combination of both is preferably shaped such as to improve coaptation with the native anterior and posterior leaflet.

The support structure is configured to carry the artificial leaflet structure and to hold the artificial leaflet structure in a position, in which it can coapt with the native second leaflet. Preferably, the artificial leaflet is held in a position closer to the native second leaflet when compared to the position of the malcoapting native first leaflet. In particular, the artificial leaflet bears against the native second leaflet and, depending on the degree of pathological dilatation of the annulus, displaces the native first leaflet to a location closer to the wall of the ventricle when compared to its original location. In some embodiments in case of a restrictive native leaflet the artificial leaflet mounts the diseased and malfunctioning native leaflet, leaving some mobility to facilitate the valve closure of the artificial valve.

In order to associate the implant to the annulus, the support structure and/or the flexible artificial leaflet structure preferably comprises fixing means for fixing the support structure and/or the flexible artificial leaflet structure to the annulus or to the native first leaflet. Preferably, the fixing means comprise a first fixing element and a second fixing element movable relative to each other so as to be able to squeeze a section of the native annulus or the native first leaflet between them.

Fixing the support structure relative to the annulus preferably comprises arranging the support element, which is preferably designed as a full ring structure at least partially within the inner circumferential surface of the annulus and expanding the upper support element in a radial direction towards the inner circumferential surface of the annulus.

In order to enable a radial expansion of the support element so as to apply a bracing force, the support structure is preferably made from a shape memory material, such as Nitinol, and preferably is in the form of a mesh or of a wire.

Preferably, the support structure is substantially U-shaped or C-shaped or semi-circular or circular so as to fit the shape of the annulus. The support structure may further comprise a collar angled radially outwardly and adapted to lie on the upstream side of the annulus.

Alternatively, the support structure is ring-shaped in order to lie against the full circumference of the annulus.

According to the invention, the rim section of the artificial leaflet is shaped to coapt with the native second leaflet, wherein said rim section comprises pockets that are open towards said downstream side and capable of being filled with blood from the downstream side each time the valve is closed. The pockets may be made from a flexible material so that the rim section of the artificial leaflet can easily adapt its shape to the corresponding counterface of the native second leaflet when the valve is closed. In this way, the coaptation is improved substantially. When the pockets, preferably comprising a honeycomb structure, get filled with blood from the downstream side of the valve, a fluid pressure is created inside the pockets, which results in that the pockets and thus the rim section of the artificial leaflet exert a pressure against the native second leaflet. The pressure inside the pockets increases with the increasing pressure prevailing in the heart ventricle so that the sealing force between the artificial leaflet and the native second leaflet increases the higher the pressure in the ventricle is.

Preferably, a plurality of pockets are arranged in at least one row forming the rim section of the artificial leaflet structure. In this way the entire length of the rim section as well as the indentations between parts of the valve (i.e. P1,P2,P3 in a posterior mitral leaflet) between the native valve consists of said pockets that can adapt to the shape of the oppositely arranged rim of the native second leaflet. The pockets of said at least one row may all have the same size, i.e. having the same blood uptake volume, or may have different sizes. In particular, pockets in a middle region of said row have a greater size, i.e. a bigger blood uptake volume, than pockets in both end regions of said row.

The at least one row of pockets forming the rim section of the artificial leaflet may be arranged such that the row of pockets protrude from the outer rim of the native first leaflet, thereby extending the area of the native first leaflet.

The pockets each may have a rounded, in particular semicircular surface for coapting with the native second leaflet. Alternatively the pockets may have an octagonal or hexagonal cross section. In this way, an alveolar configuration of the pockets is achieved.

Further, the artificial leaflet structure may preferably comprise a base section arranged between the rim section and the support structure. The base section of the artificial leaflet forms that part of the artificial leaflet that is attached to the support structure and, on the side that is arranged to coapt with the native second leaflet, carries the rim section that comprises the plurality of pockets. In addition, the plurality of pockets supports the artificial leaflet, preventing it from prolapsing into the atrium.

The base section may be designed as a flexible sheet or web or honeycomb structure or leaf and thus form a two-dimensional structure. Alternatively, the base section, such as the rim section, may be designed as a three-dimensional structure, such as three-dimensional web structure, wherein the base section preferably comprises pockets that are open towards said downstream side and capable of being filled with blood from the downstream side as the valve closes. Alternatively, the base section comprises at least one closed cavity designed to be filled with a filling material different from blood. The closed cavity when being filled with a filling material may expand to a defined shape and volume. Once expanded, the artificial leaflet structure has an increased structural stability and may adopt a defined surface shape. The artificial leaflet structure may comprise several cavities that are connected with each other and are mounted and fixed on the native valve. The filling material may be selected from the group consisting of a fluid, an elastic solid, such as a foamed material, and a gel. The cavity preferably comprises a closable opening for filling the cavity with the filling material. The filling material is preferably filled into the cavity after the implant has been deployed to the heart. Alternatively, the artificial leaflet is expanded by expanding a filling material contained in the cavity. In this case, the filling material may be already present in the cavity before the implant is deployed to the heart and may be expanded by filling the cavity with serum via a semipermeable part of the cavity wall. The filling material may be a liquid that forms a foamed structure as soon as a chemical reaction is initiated by applying heat, radiation, water or the like. In some embodiments the filled semi-flexible material is sculptured by the mechanical force of the second leaflet within the first closing attempts until the filled material receives its permanent shape. In some embodiments a semipermeable structure of the textile of the compartments allow the penetration of a plasma-like fluid that might react with substances filling the compartments.

In some embodiments, the invention provides an implant for improving coaptation of an atrioventricular valve, the implant comprising a support structure and a flexible artificial leaflet structure mounted to the support structure and shaped to coapt with the native second leaflet, wherein the support structure and the artificial leaflet structure are deployable from a first position, in which the support structure and the artificial leaflet structure are arranged within a tubular housing, into a second position, in which the artificial leaflet structure is deployed to coapt with the second native leaflet. In this way, the implant can be easily deployed to the heart by transvascular, transcatheter and minimal invasive procedures or surgery. In particular, the tubular housing is preferably advanced into the heart by means of a catheter transatrially, transseptally, transfemorally or transapically.

Preferably, the support structure and the artificial leaflet structure are configured to be deployed from a folded or rolled-up state into an extended state. In the folded or rolled-up state, the structures may easily be advanced to the heart transcatheterally.

The artificial leaflet may be made of a biocompatible material, such as polyethylene or polyurethane, polyfluorethylen (Goretex®) or from natural tissue such as heterologic pericardium. The artificial leaflet may be made by 3D printing of PTFE according to pre-implantation imaging data obtained by using 4D echocardiography and fusion imaging with Cardio CT and MRI.

Preferably, the implant further comprises retention means connected to the support structure and the artificial leaflet for preventing prolapse of the artificial leaflet. In particular, the retention means may be flexible in order to allow the artificial leaflet to perform its usual function and coapt with the native second leaflet.

Preferably, the retention means, on one end thereof, are connected to the support structure and, on the other end thereof, are connected to the artificial leaflet structure.

The retention means may comprise a flexible net or a plurality of flexible wires or yarns. The flexible net, wires or yarns may be embedded into or fixed to the artificial leaflet structure.

According to a further aspect the invention refers to a method of improving coaptation of an atrioventricular valve, the atrioventricular valve having an annulus, a native first leaflet and a native second leaflet, the method comprising:
  providing an implant comprising a support structure and
    a flexible artificial leaflet structure mounted to the
    support structure, the implant being arranged in a
    tubular housing,
  advancing the tubular housing by means of a catheter
    through a body vessel of a patient into the heart,
  deploying the implant from the tubular housing,
  fixing the support structure relative to the annulus or the
    native first leaflet so that the artificial leaflet structure
    can coapt with the native second leaflet,
  preferably fitting the semicircular or circular support
    structure within the valve annulus with an expandable
    structure,
  preferably fixing the semicircular or circular support ring
    structure with elements penetrating into the tissue for
    holding the ring in place.

Preferably, the native first leaflet is a native posterior leaflet of a mitral valve and the second native leaflet is an anterior leaflet of the mitral valve. The artificial leaflet is configured as an artificial posterior leaflet and replaces the normal function of the native posterior leaflet. The artificial posterior leaflet is preferably shaped such as to improve coaptation with the native anterior leaflet.

Preferably, the tubular housing is advanced into the heart by means of a catheter transatrially, i.e. through the left atrium of the heart, transseptally, i.e. through the septum of the heart, transfemorally or transapically, i.e. through the apex of the heart. The positioning is facilitated by a steerable guiding element to maneuver the deployable element into the rim of the annulus connecting the ventricular wall with the leaflet structure.

Preferably, the step of fixing the support structure relative to the annulus comprises arranging the support structure at least partially within the inner circumferential surface of the annulus and expanding the support element in a radial direction towards the inner circumferential surface of the annulus.

Preferably, the artificial leaflet structure is expanded by filling a filling material into the at least one cavity provided in the base section of the artificial leaflet structure.

Preferably, the method further comprises connecting the artificial leaflet to the support structure by the aid of retention means for preventing prolapse of the artificial leaflet.

Instead of fixing the support structure onto the annulus, the support structure may alternatively also be fixed onto the native first leaflet.

In some embodiments, the invention provides a method comprising the steps of
imaging the native mitral valve prior to the procedure,
identifying and localizing the areas of malcoaptation,
measuring leaflet heights in all three scallops (p1,p2,p3) and their form and the two indentations,
measuring the extend of the posterior leaflet,
virtual reconstructing of an artificial posterior leaflet with scallops and artificial chordae,
implementing the patient's mitral valve into a computer model, thereby obtaining 3D data of the mitral valve,
adapting the 3D data in the computer model to improve coaptation,
using the adapted 3D data from the computer model to obtain 3D data representative of the three scallops as well as of the wall coverage of the posterior leaflet,
3D printing of artificial scallops of the posterior leaflet from said 3D data,
using the artificial scallops as a model and building an artificial posterior leaflet on said model, optionally including modeling cushion sizes and forms for the definite coaptation surface area,
connecting the artificial posterior leaflet to a support structure,
folding the support structure and the artificial leaflet and arranging the same into a tubular housing,
delivering the tubular housing by means of a catheter transatrially, transseptally, transfemorally or transapically to the mitral valve of the heart,
anchoring the support structure to the native mitral valve.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
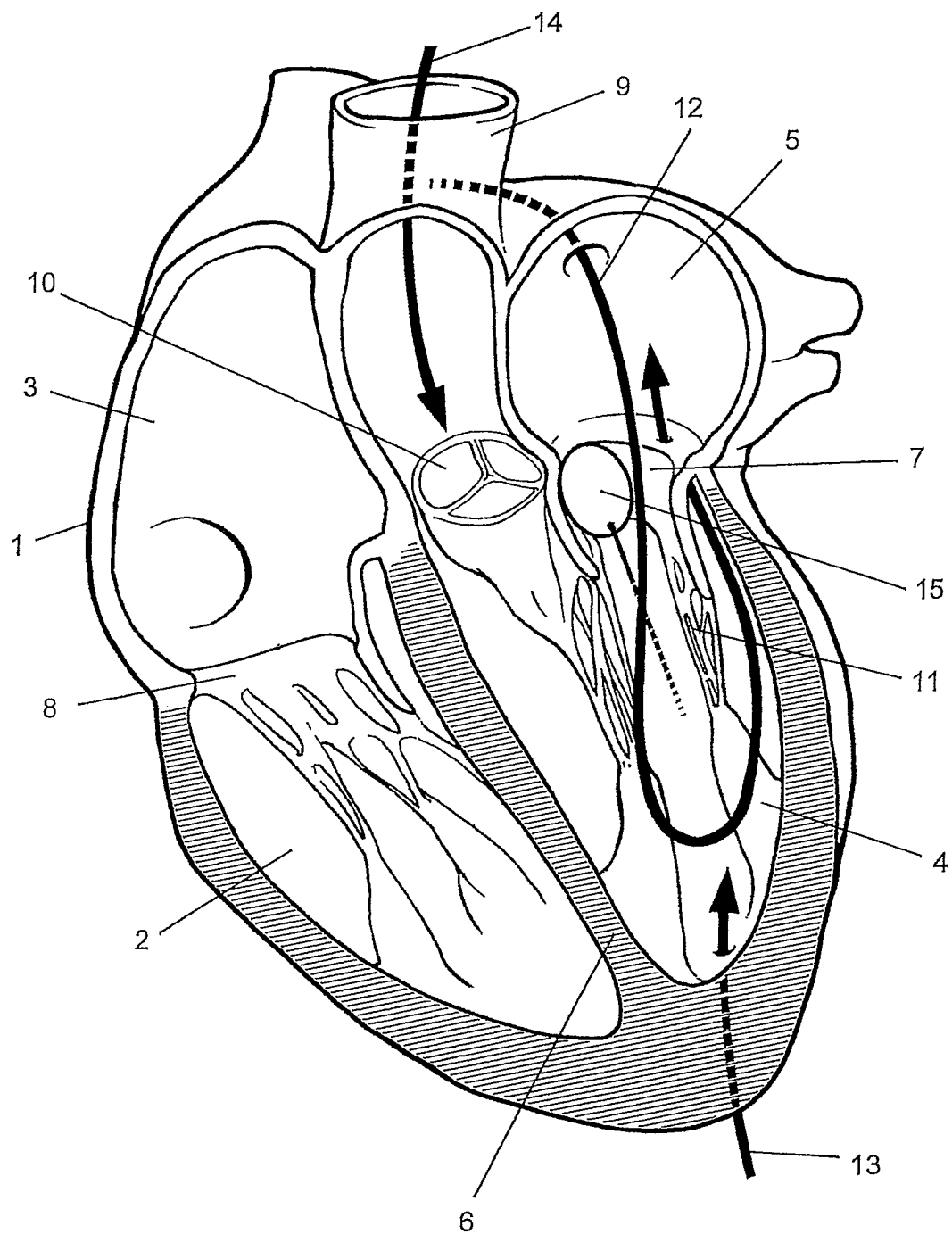
FIG. 1 is a schematic illustration of a human heart.

FIG. 1 is a schematic illustration of a human heart 1 comprising the right ventricle 2, the right atrium 3, the left ventricle 4 and the left atrium 5. The septum 6 divides the heart 1 in a right and a left section. The mitral valve 7 allows the blood to flow from the left atrium 5 into the left ventricle 4. The tricuspid valve 8 is located between the right atrium 3 and the right ventricle 2. The ascending aorta 9 originates at the orifice of the aortic valve 10. The mitral valve 7 comprises an anterior leaflet and a posterior leaflet that are anchored within the left ventricular cavity by chordae tendineae 11, which prevent the valve 7 from prolapsing into the left atrium 5.

The mitral valve implant of the invention is configured to be deployed to the heart transcatheterally. In particular, the implant can be delivered to the heart by means of a catheter transatrially, i.e. through the left atrium of the heart, transseptally, i.e. through the septum 6 of the heart as depicted by line 12, transapically, i.e. through the apex of the heart as depicted by line 13, or through the ascending aorta 9 as depicted by line 14.

During the implant procedure a balloon 15 may be placed into the orifice of the mitral valve 7, which is inflated during systole and deflated during diastole to minimize regurgitant volume flow and to prevent severe inflow into the pulmonary veins.

Figure 2:
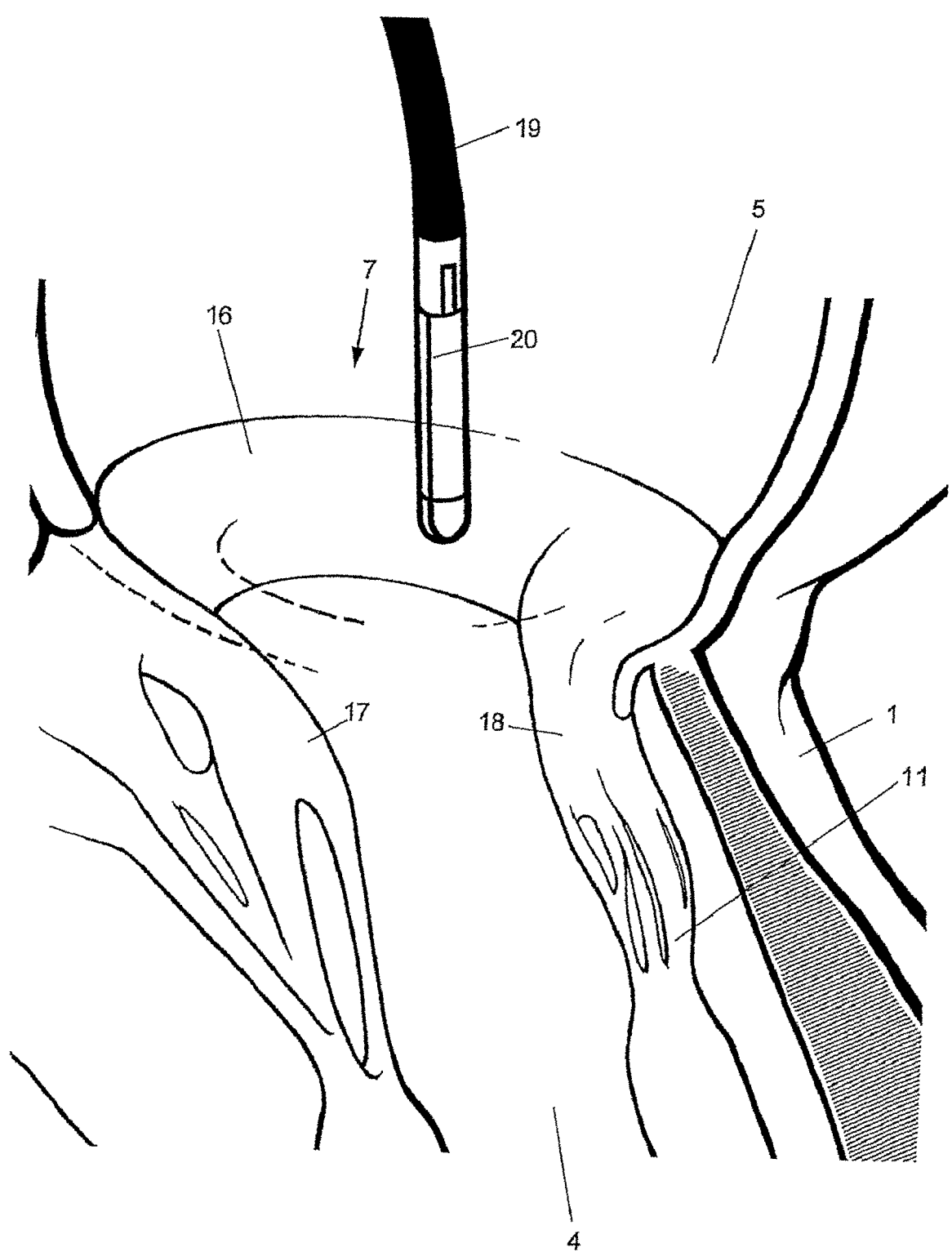
FIG. 2 is a schematic illustration of the region of the mitral valve of the heart with an implant being advanced to the valve in a tubular housing.

In FIG. 2 the mitral valve 7 is shown in more detail. The mitral valve 7 comprises an annulus 16, from which the anterior leaflet 17 and the posterior leaflet 18 emerge. In a pathological condition of the mitral valve 7, the annulus 16 can be dilated so that the anterior leaflet 17 and the posterior leaflet 18 fail to coapt and do not provide a tight seal between the left ventricle 4 and the left atrium 5 during systole. A catheter 19 is shown that has been advanced into the left ventricle 4. The catheter carries a tubular housing 20 on its free end, in which the implant is arranged in a compacted, in particular folded state during delivery. The mitral implant can be deployed as later shown in FIGS. 7, 8 and 9.

Figure 3:
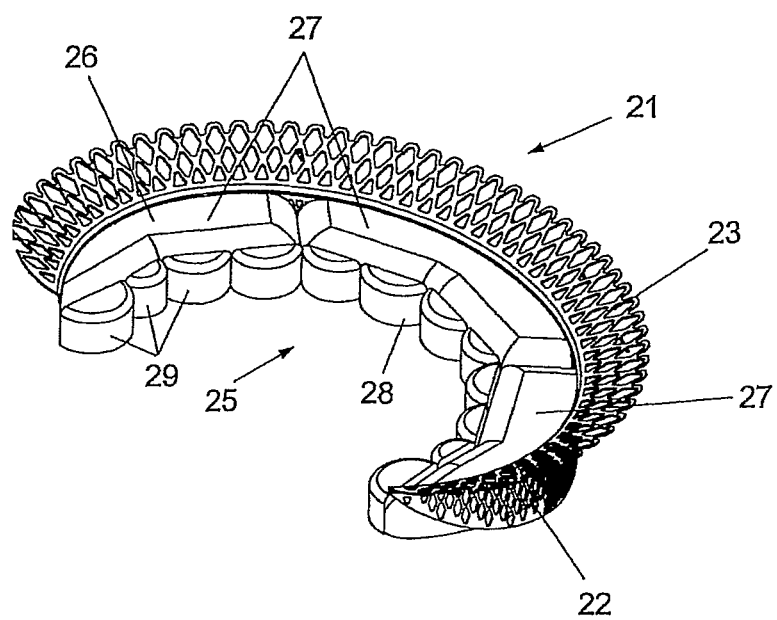
FIG. 3 is a schematic illustration of a first exemplary embodiment of a mitral valve implant in a perspective view.
Figure 4:
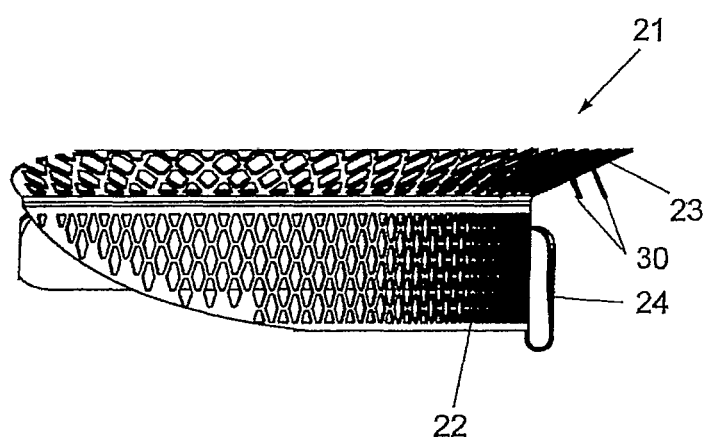
FIG. 4 is a schematic illustration of the first exemplary embodiment of a mitral valve implant in a side view.

In FIG. 3 the mitral implant is shown in a perspective view. The implant comprises a support structure 21, which is made from a meshed memory shape material, such as Nitinol. As can be better seen in the side view according to FIG. 4 the support structure 21 comprises a cylindrical main section 22 and an upper section 23 that is in the form of a collar that is angled radially outwardly. The support structure 21 has a generally C-shaped form as can be seen in the top view according to FIG. 5. The main section 22 and the upper section 23 of the support structure 21 are adapted to lie on the inner circumference and on the upstream side of the annulus 16 respectively. The support structure 21 is generally shaped to conform to the curvature of the annulus 16.

The support structure 21 may comprise mechanical securing means, such as harpoon like needles 30 with hooks, which are deployed to penetrate into the annulus to secure the seating of the support structure 21.

Figure 6:
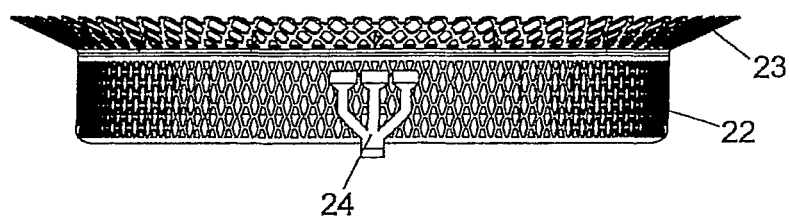
FIG. 6 is a schematic illustration of the first exemplary embodiment of a mitral valve implant in a back view.

The fixing means for fixing the support structure 21 onto the annulus or the native posterior leaflet 18 is denoted by 24 and can be seen in the rear view according to FIG. 6. The fixing means is designed in the form of a resilient clamp so that the annulus 16 or the native posterior leaflet can be clamped between the clamp 24 and the main section 22 of the support structure 21. The fixing means is arranged in the symmetry plane of the implant, namely on the outer side of the support structure 21.

Figure 5:
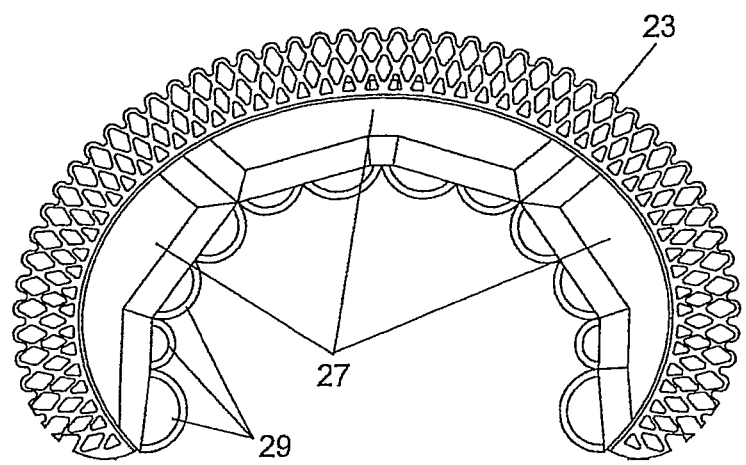
FIG. 5 is a schematic illustration of the first exemplary embodiment of a mitral valve implant in a top view.

An artificial leaflet 25 is attached to the inner circumference of the support structure 21 as can be seen in the perspective view according to FIG. 3 and in the top view according to FIG. 5. The artificial leaflet 25 comprises a base section 26 immediately adjacent the support structure 21, in which the artificial leaflet 25 comprises a plurality of cushion-like embossments 27 mimicking the natural shape of the scallops (p1,p2,p3) of the native posterior leaflet 18. Further, the artificial leaflet 25 comprises a rim section 28 that comprises a plurality of pockets 29 that are open towards said downstream side of the valve 7, which is the lower side in FIGS. 3 and 4. The pockets 29 are capable of being filled with blood from the downstream side each time the valve 7 is closed. The pockets 29 are arranged in a row thereby forming the rim section of the artificial leaflet 25. As can be seen in FIG. 3 and in FIG. 5 the pockets each have a rounded, in particular semicircular surface for coapting with the anterior leaflet 17. In another arrangement the pockets can be supported with a web structure forming octagons or similar geometric figures.

Figure 7:
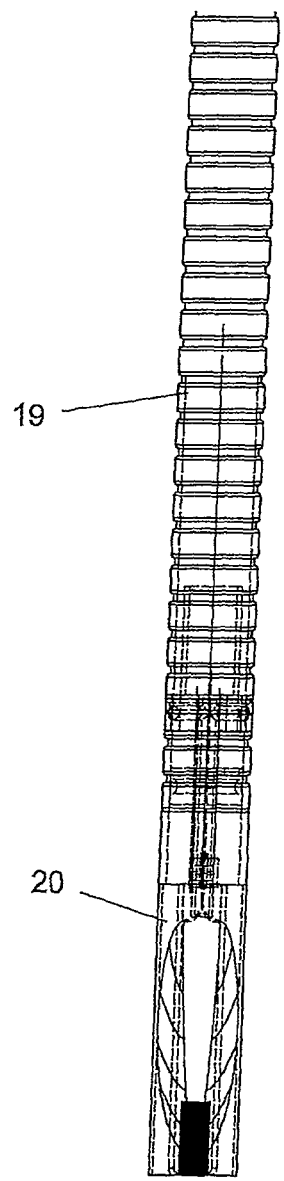
FIG. 7 is a schematic illustration of an exemplary embodiment of a mitral valve implant in a folded state.

FIG. 7 shows the implant folded so that it may be housed in the tubular housing 20 before being deployed. In its folded state, the implant may be arranged in a catheter 19 and advanced into the left ventricle of the heart.

Figure 8:
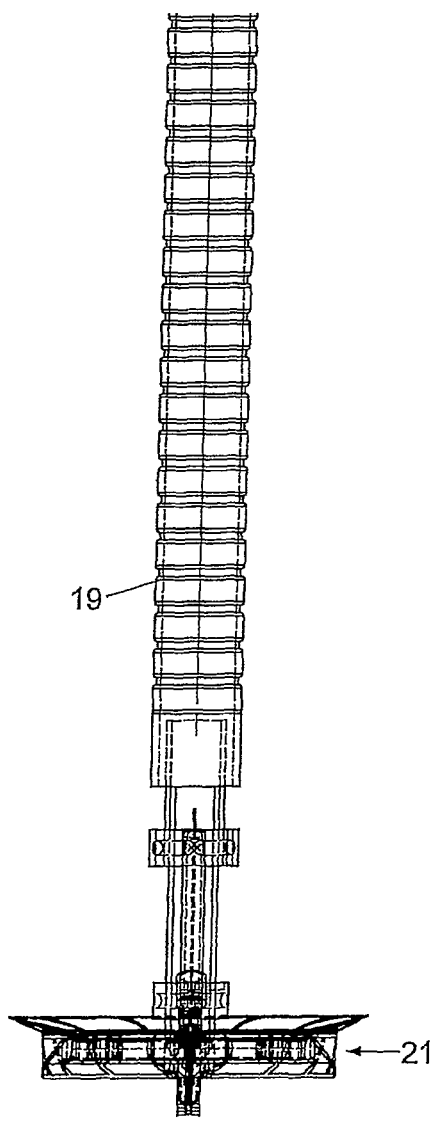
FIG. 8 is a schematic illustration of an exemplary embodiment of a mitral valve implant in a deployed state in a front view.
Figure 9:
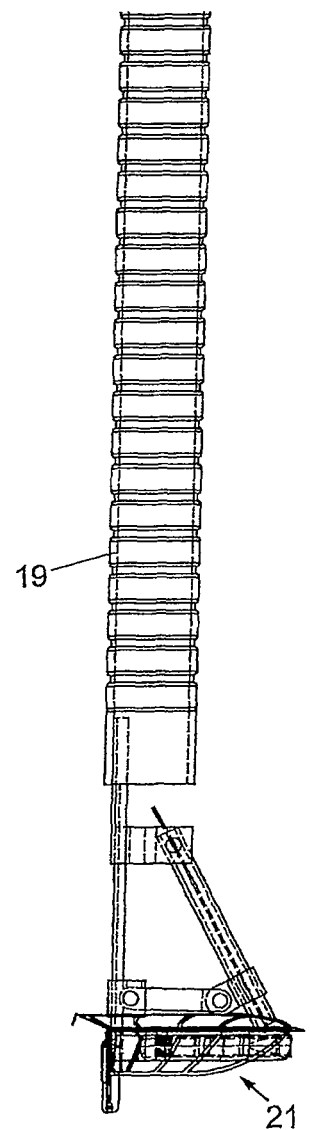
FIG. 9 is a schematic illustration of an exemplary embodiment of a mitral valve implant in a deployed state in a side view.

Starting from its folded state according to FIG. 7, a deployment procedure can be applied to deploy the implant into its full size as shown in FIG. 8. FIG. 9 is a side view of the deployed implant of FIG. 8 and shows that unfolding occurs by unfolding the semicircular or circular support structure from a looping vertical position into a horizontal plane just before deployment of harpoons or other mechanical fixation means.

Figure 10:
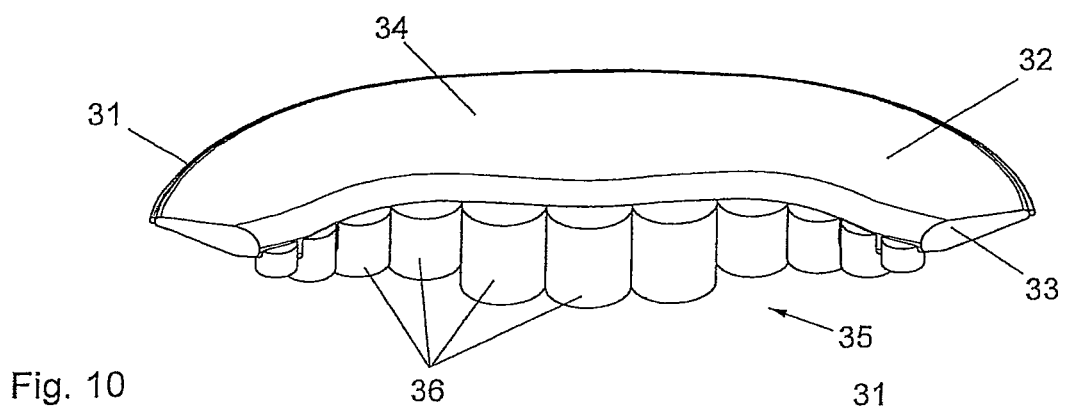
FIG. 10 is a schematic illustration of a second exemplary embodiment of a mitral valve implant in a perspective view from above.
Figure 11:
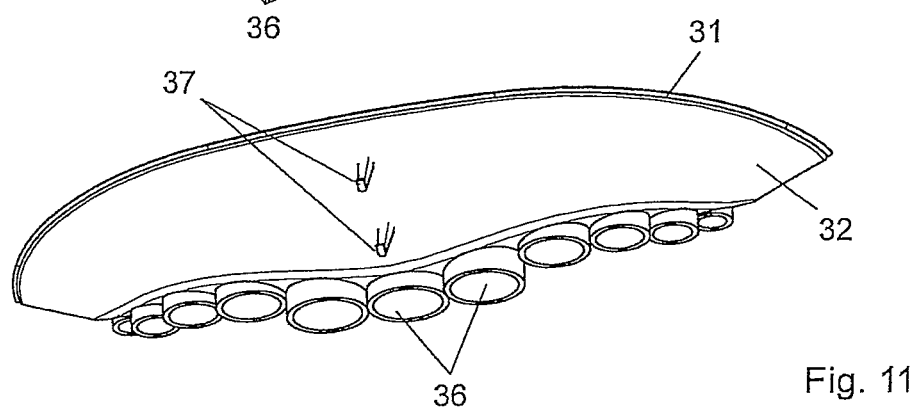
FIG. 11 is a schematic illustration of the second exemplary embodiment of a mitral valve implant in a perspective view from below.
Figure 12:
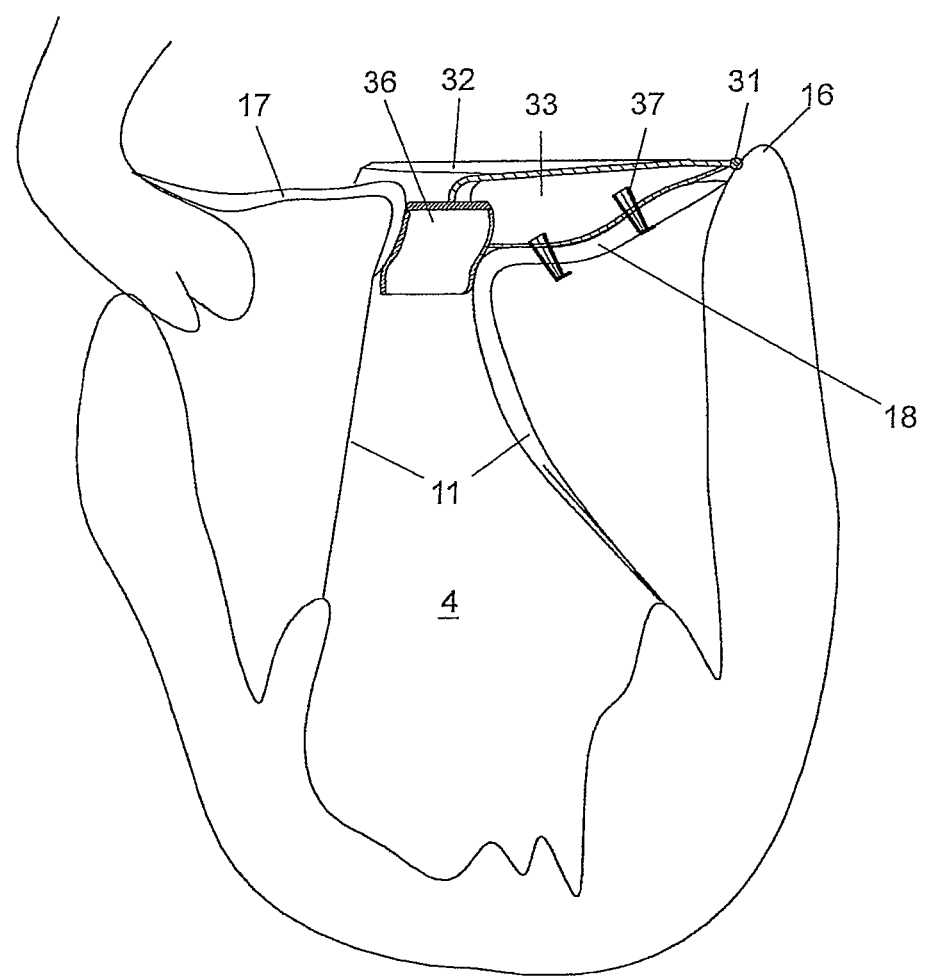
FIG. 12 is a cross sectional view of a mitral valve with the mitral valve implant of the second exemplary embodiment being installed.

In FIGS. 10 and 11 the mitral implant is shown in a perspective view. The implant comprises a support structure 31, which is made from a meshed memory shape material, such as Nitinol. The support structure 31 has a generally C-shaped form and is adapted to rest on the inner circumference of the annulus 16. The support structure 31 is generally shaped to conform to the curvature of the annulus 16. As shown in FIGS. 10 and 11, the pockets in a center of the rim section have a greater cross-section than the pockets in side regions of the rim section.

An artificial leaflet 32 is attached to the support structure 31. The artificial leaflet 32 comprises a base section 34 immediately adjacent the support structure 31, in which the artificial leaflet 32 has a three-dimensional shape having a cavity 33. Further, the artificial leaflet 32 comprises a rim section 35 that comprises a plurality of pockets 36 that are open towards the downstream side of the valve 7. The pockets 36 are capable of being filled with blood from the downstream side each time the valve 7 is closed. The pockets 36 are arranged in a row thereby forming the rim section of the artificial leaflet 32. The pockets each have a rounded, in particular semicircular surface for coapting with the anterior leaflet 17.

The base section 34 of the artificial leaflet 32 is arranged on the upper surface of the native posterior leaflet 18 and is fixed to the posterior leaflet 18 with fixing means. The fixing means are designed in the form of two or more pins 37 that penetrate the posterior leaflet 18. In particular, the fixing means may comprise fixing elements, such as a pin 37 and a counter element engaging the pin 37, wherein the posterior leaflet 18 is squeezed between said fixing elements.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. An implant for improving coaptation of an atrioventricular valve, the atrioventricular valve having a native first leaflet, a native second leaflet and an annulus and controlling blood flow from an upstream atrial side to a downstream ventricular side of the valve, the implant comprising:
a support structure configured to be fixed to the annulus or to the native first leaflet; and
a flexible artificial leaflet structure mounted to the support structure and comprising a rim section that is shaped to coapt with the native second leaflet such that a gap between the native first leaflet and the native second leaflet is closed,
wherein said rim section is configured to be arranged in the gap between the native first leaflet and the native second leaflet and comprises a plurality of pockets that are open towards said downstream ventricular side and capable of being filled with blood from the downstream ventricular side each time the valve is closed; and wherein the pockets in a center of the rim section have a greater cross-section than the pockets in side regions of the rim section.

2. The implant according to claim 1, wherein the plurality of pockets are arranged in at least one row forming the rim section of the artificial leaflet structure.

3. The implant according to claim 1, wherein the pockets each have a rounded surface for coapting with the native second leaflet.

4. The implant according to claim 1, wherein the artificial leaflet structure comprises a base section arranged between the rim section and the support structure.

5. The implant according to claim 4, wherein the base section comprises pockets that are open towards said downstream ventricular side and capable of being filled with blood from the downstream ventricular side or at least one closed cavity designed to be filled with a filling material different from blood.

6. An implant delivery and deployment device, comprising:
the implant according to claim 1; and
a tubular housing, wherein the support structure and the artificial leaflet structure are deployable from a first position, in which the support structure and the artificial leaflet structure are arranged within the tubular housing, into a second position, in which the support structure is deployed and the artificial leaflet structure is deployed to coapt with the native second leaflet.

7. The implant according to claim 1, wherein the support structure is substantially U-shaped, C-shaped or semi-circular or circular so as to fit the shape of the annulus.

8. The implant according to claim 1, wherein the support structure is made from a shape memory material.

9. The implant according to claim 1, wherein the support structure comprises a collar angled radially outwardly and adapted to lie on the upstream atrial side of the annulus.

10. The implant according to claim 1, the implant further comprising retention means fixed to the support structure so as to prevent prolapse of the artificial leaflet structure.

11. The implant according to claim 10, wherein the retention means, on one end thereof, are connected to the support structure and, on the other end thereof, are connected to the artificial leaflet structure.

12. The implant according to claim 10, wherein the retention means comprise a flexible net or a plurality of flexible wires or yarns.

13. The implant according to claim 12, wherein the flexible net, wires or yarns are embedded into or fixed to the artificial leaflet structure.

14. The implant according to claim 1, wherein the support structure comprises fixing means for fixing the support structure to the annulus or to the native first leaflet.

15. The implant according to claim 14, wherein the fixing means comprise a first fixing element and a second fixing element movable relative to each other so as to be able to squeeze a section of the native annulus or the native first leaflet between them.

16. The implant according to claim 1, wherein a) the atrioventricular valve is a mitral valve and the first native leaflet is a posterior leaflet of the mitral valve orb) the atrioventricular valve is a tricuspid valve and the first native leaflet is an anterior or posterior leaflet of the tricuspid valve.

17. A method of improving coaptation of an atrioventricular valve, the atrioventricular valve having an annulus, a native first leaflet and a native second leaflet, the method comprising:
providing an implant for controlling blood flow from an upstream atrial side to a downstream ventricular side of the valve, the implant comprising:
a support structure configured to be fixed to the annulus or to the native first leaflet; and
a flexible artificial leaflet structure mounted to the support structure and comprising a rim section that is shaped to coapt with the native second leaflet such that a gap between the native first leaflet and the native second leaflet is closed,
wherein said rim section is configured to be arranged in the gap between the native first leaflet and the native second leaflet and comprises a plurality of pockets that are open towards said downstream ventricular side and capable of being filled with blood from the downstream ventricular side each time the valve is closed, and
wherein the pockets in a center of the rim section have a greater cross-section than the pockets in side regions of the rim section;
wherein the implant is arranged in a tubular housing, advancing the tubular housing by means of a catheter through a body vessel of a patient into the heart;
deploying the implant from the tubular housing; and
fixing the support structure relative to the annulus or the native first leaflet so that the artificial leaflet structure can coapt with the native second leaflet.

18. The method according to claim 17, wherein the tubular housing is advanced into the heart by means of a catheter transatrially, transseptally, transfemorally or transapically.

19. The method according to claim 17, wherein the step of fixing the support structure relative to the annulus comprises arranging the support structure at least partially within the inner circumferential surface of the annulus and expanding the support element in a radial direction towards the inner circumferential surface of the annulus.

20. The implant according to claim 3, wherein the rounded surface of the pockets is semicircular.

21. The implant according to claim 8, wherein the shape memory material is Nitinol and is at least in part in a form of a mesh.

* * * * *